United States Patent [19]
Atsumi et al.

[11] Patent Number: 5,266,534
[45] Date of Patent: Nov. 30, 1993

[54] ANTIBACTERIAL CALCIUM PHOSPHATE CERAMIC

[75] Inventors: Kiminori Atsumi; Tomoki Saito; Masaaki Komori, all of Tokyo, Japan

[73] Assignee: Kabushiki Kaisha Sangi, Tokyo, Japan

[21] Appl. No.: 871,658

[22] Filed: Apr. 21, 1992

[30] Foreign Application Priority Data

Nov. 5, 1991 [JP] Japan .................................. 3-315222

[51] Int. Cl.$^5$ ...................... C04B 35/00; A01N 59/26; A01N 59/16
[52] U.S. Cl. ...................................... 501/1; 106/18.31; 106/18.36; 106/35; 106/462; 424/602; 424/618; 424/641; 424/724
[58] Field of Search ............... 501/1; 106/18.31, 18.36, 106/35, 462; 502/150, 232, 243, 174, 214; 424/602, 618, 641, 724

[56] References Cited

U.S. PATENT DOCUMENTS

| | | | |
|---|---|---|---|
| 3,194,730 | 7/1965 | Nemec et al. | 167/42 |
| 3,926,646 | 12/1975 | Inoue | 106/35 |
| 4,778,471 | 10/1988 | Bajpai | 501/1 |
| 4,988,362 | 1/1991 | Toriyama et al. | 501/1 |
| 5,009,898 | 4/1991 | Sakuma et al. | 106/35 |
| 5,017,518 | 5/1991 | Hirayama et al. | 106/35 |
| 5,151,122 | 9/1992 | Atsumi et al. | 106/35 |

FOREIGN PATENT DOCUMENTS 2238044 5/1991 United Kingdom .

OTHER PUBLICATIONS

Derwent Japanese Patents Report, d. Feb. 6, 1992, Derwent Publications Ltd., London, GB & JP-A-3 036 220 (Catalysts & Chem. Ind. Co. Ltd.) (Abstract).
Database WPIL Week 8831, Dec. 13, 1986 Derwent Publications Ltd., London, GB; AN 88-216265 & JP-A-63 151 644 (Kyushu Refractories) Abstract.

*Primary Examiner*—Mark L. Bell
*Assistant Examiner*—Deborah Jones
*Attorney, Agent, or Firm*—Finnegan, Henderson, Farabow, Garrett & Dunner

[57] ABSTRACT

A calcium phosphate ceramic such as hydroxyapatite or calcium tertiary phosphate or calcium carbonate is used as a carrier, and the carrier is caused to carry silicon in addition to silver, or silicon and zinc in addition to silver. The result is an antibacterial ceramic exhibiting an ultra high degree of whiteness and suppressed discoloration. This ceramic material may be heat-fired at a temperature above 960° C. to obtain a further improvement.

9 Claims, No Drawings

ANTIBACTERIAL CALCIUM PHOSPHATE CERAMIC

BACKGROUND OF THE INVENTION

1. Field of the Invention

This invention relates to an antibacterial calcium phosphate ceramic and antibacterial calcium carbonate. More particularly, the invention relates to a calcium phosphate ceramic and calcium carbonate made to carry silver and silicon and/or ions thereof or silver, silicon and zinc and/or ions thereof, wherein the calcium phosphate ceramic and calcium carbonate are safe, exhibit a high degree of whiteness and resist discoloration to the maximum extent.

2. Description of the Prior Art

It is known that metals such as silver and zinc as well as ions and salts of these metals exhibit a strong antibacterial property, and various processes have been proposed for utilizing these. However, when these metals are used as is in mixture with a substrate such as resin, fibers or paint, problems arise involving dispersibility with respect to the substrate, the eluting property of the metal ions, tinting and discoloration. For this reason, use in wide fields of application has not been possible.

Substances in which antibacterial metals, metal salts or metal ions are carried on highly safe ceramics such as zeolite, calcium secondary phosphate and hydroxyapatite have recently been proposed as substances which utilize the antibacterial property of the above-mentioned metals. Since these substances exhibit reduced elution of the carried antibacterial metal ions into water and have improved dispersibility with respect to the substrate, they can be utilized comparatively safely and in many fields of application. However, depending upon the medium used, even these substances undergo elution of their metal ions into the medium, and therefore they cannot always be used with complete safety in all types of media. Moreover, it is known that silver generally is sensitive to light and will break down and change color to gray or black when exposed to light. Accordingly, silver salts undergo discoloration when used as is. Antibacterial agents in which this metal salt is carried on ceramics or the like can lead to problems not only in terms of discoloration but also in terms of safety since the elution of silver from the silver salt and the release of silver salt from the ceramics cannot be reasonably prevented.

Though zeolite made to carry silver by means of ion exchange exhibits less discoloration in comparison to those cases where the silver salt is used as is, discoloration with the passage of time is unavoidable. In comparison with zeolite carrying silver, hydroxyapatite made to carry silver by ion exchange is much improved in terms of discoloration attributable to the silver, but complete suppression of discoloration has still not realized, and the degree of whiteness is not to a high degree even before discoloration can occur. In a case where calcium primary phosphate, calcium secondary phosphate or calcium pyrophosphate is used alone as the carrier, there is little improvement with regard to the elution of silver and discoloration.

Studies have been conducted with a view to improving upon the foregoing, and processes for carrying zinc along with silver and for heat-firing have been considered. However, in a case where zinc is carried together with silver, the antibacterial agent tends to become a light gray in color as the amount of silver carried is increased, and even though the color is near white, the degree of whiteness is low. In addition, discoloration cannot be completely suppressed over an extended period of time. In a case where heat-firing is carried out, discoloration can be suppressed. Nevertheless, the antibacterial agent itself still becomes light brown in color and the degree of whiteness diminishes as the amount of silver carried increases. These problems arise when silver is used as the antibacterial metal, and though improvements have been made, they still have not been resolved totally.

SUMMARY OF THE INVENTION

Accordingly, an object of the present invention is to provide antibacterial calcium phosphate and antibacterial calcium carbonate, which exhibit a high degree of whiteness and will not undergo discoloration even when stored for very long periods of time, and in which safe calcium phosphate and calcium carbonate are used as the carrier, and wherein silver, which exhibits the strongest antibacterial property among the metals, is adopted as the antibacterial substance.

As mentioned above, an antibacterial agent obtained by having hydroxyapatite carry silver and zinc or by being heat-fired is an easy-to-use antibacterial material which also exhibits excellent dispersibility in substrates, discoloration has been seen with the passage of time, and the antibacterial agent becomes light brown in color as a result. As a consequence, problems arise in terms of storage of the antibacterial agent and the color of manufactured articles produced with use of the agent, and therefore the fields of application are limited.

Accordingly, the inventors have devoted research to silver-containing inorganic antibacterial agents which exhibit an ultra high degree of whiteness and will not undergo discoloration. As a result of this research, the inventors have been able to obtain an antibacterial agent which attains the foregoing object. Specifically, by using a calcium phosphate ceramic such as hydroxyapatite or calcium tertiary phosphate or calcium carbonate as the carrier and causing this carrier to carry silicon in addition to silver or silicon and zinc in addition to silver, an antibacterial agent exhibiting an ultra high degree of whiteness and substantially suppressed discoloration has been obtained. By heat-firing a calcium phosphate ceramic, which has been made to carry silicon in addition to silver or silicon and zinc in addition to silver, at a temperature above 960° C., an antibacterial agent which exhibits a superior degree of whiteness higher than that of the substance not heat-fired, and which will not undergo discoloration, has been obtained.

More specifically, a prescribed amount of calcium tertiary phosphate is added to an aqueous solution of a soluble silver salt and a silicon ingredient such as silicon dioxide or methyl silicate, to which a prescribed amount of a soluble zinc salt is added as necessary. The mixture is stirred. After sufficient stirring, precipitates are filtered out and the product is washed thoroughly with distilled water and then dried, whereby there is obtained antibacterial calcium tertiary phosphate. Other antibacterial calcium phosphate ceramics, such as antibacterial hydroxyapatite and antibacterial calcium secondary phosphate, as well as antibacterial calcium carbonate, also can be obtained in the same manner.

The degree of whiteness of the obtained antibacterial calcium phosphate ceramics and antibacterial calcium carbonate naturally is influenced by the amount of silver carried, just as it is influenced by the adsorption retention ratio of the silver, silicon and zinc. That is, in order to obtain an antibacterial calcium phosphate ceramic or antibacterial calcium carbonate exhibiting a superior high degree of whiteness and no change in color with the passage of time, the amount of silver adsorbed and retained should be no more than 10% by weight, and preferably no more than 5% by weight, with respect to the calcium phosphate ceramic or calcium carbonate. On the other hand, in consideration of antibacterial capability, the amount of silver retained preferably is no less than 0.0001%. A change in color with the passage of time can be suppressed even further by heat-firing the product at a temperature above 960° C., which is the melting point of silver. The amount of silicon retained in coexistence with silver is required to be at least 5% by weight with respect to the amount of silver retained. In addition, the amount of zinc retained together with silver and silicon is required to be at least 5% by weight with respect to the amount of silver retained. The amount of silicon or zinc retained can be selected at will. The silicon and zinc contribute greatly to the whitening and to the prevention of discoloration. In particular, the silicon is required for whitening and the zinc is required in preventing discoloration.

DETAILED DESCRIPTION OF THE INVENTION

An example of the present invention will now be described in detail.

EXAMPLES

One kilogram of a calcium phosphate ceramic such as hydroxyapatite, calcium tertiary phosphate, calcium secondary phosphate or calcium pyrophosphate or calcium carbonate was suspended in 10 l of distilled water, a silver ingredient such as silver nitrate or silver sulfate, a silicon ingredient such as silicon dioxide or methyl silicate, and a zinc ingredient such as zinc nitrate or zinc sulfate, and zinc phosphate were added to the suspension in prescribed amounts, and the mixture was stirred. It should also be understood within the scope of this invention that, as alternative carriers to those above-mentioned, zirconium phosphate, titanium phosphate, and zinc phosphate with the addition of a silver and a silicone as those described above and added by said suspension and stirring method may equally be used. The product was filtered out, washed thoroughly with distilled water and dried, and a portion of the resulting product was powdered to obtain an antibacterial calcium phosphate ceramic or antibacterial calcium carbonate carrying silver and silicon (Examples 1~9 —1) or silver, silicon and zinc (Examples 1~9 —2). The remainder of the product was heat-fired at 960°–1,200° C. and powdered to obtain an antibacterial calcium phosphate ceramic carrying silver and silicon (Examples 1~9 —3) or silver, silicon and zinc (Examples 1~9 —4). As a control, an antibacterial calcium phosphate ceramic or antibacterial calcium carbonate carrying silver (Controls 1~9 —1) or silver and zinc (Controls 1~9 —2) was obtained by the same process. The remainder of this product was heat-fired at 960°–1,200° C. and powdered to obtain an antibacterial calcium phosphate ceramic carrying silver (Controls 1~9 —3) or silver and zinc (Controls 1~9 —4). With regard to the actual amounts of silver, silicon and zinc added, the proportions were as follows, by way of example: Approximately 18 g of silver nitrate was used in order to carry 1% of silver; approximately 24 g of silicon dioxide (when this was employed as the silicon ingredient) or approximately 84 ml of methyl silicate (when this was employed as the silicon ingredient) was used in order to carry 1% of silicon, and approximately 48 g of zinc nitrate was used in order to carry 1% of zinc).

The antibacterial agents produced by the foregoing process are indicated in Table 1.

TABLE 1

| SAMPLE | CARRIER | AMOUNTS CARRIED (WT-%) | | | FIRING TEMPERATURE |
|---|---|---|---|---|---|
| | | Ag | Si | Zn | |
| Ex. 1-1 | HYDROXY- | 0.00011 | | | UNFIRED |
| Cont. 1-1 | APATITE | 0.0001 | | | |
| Ex. 1-2 | | 0.00011 | 0.5 | | |
| Cont. 1-2 | | 0.0001 | 0.5 | | |
| Ex. 1-3 | | 0.00011 | | | 960° C. |
| Cont. 1-3 | | 0.0001 | | | |
| Ex. 1-4 | | 0.00011 | 0.5 | | |
| Cont. 1-4 | | 0.0001 | 0.5 | | |
| Ex. 2-1 | CALCIUM | 0.1 | 0.05 | | UNFIRED |
| Cont. 2-1 | TERTIARY | 0.1 | | | |
| Ex. 2-2 | PHOSPHATE | 0.1 | 0.005 | 0.005 | |
| Cont. 2-2 | | 0.1 | | 0.005 | |
| Ex. 2-3 | | 0.1 | 0.005 | | 1000° C. |
| Cont. 2-3 | | 0.1 | | | |
| Ex. 2-4 | | 0.1 | 0.005 | 0.005 | |
| Cont. 2-4 | | 0.1 | | 0.005 | |
| Ex. 3-1 | CALCIUM | 0.1 | 0.5 | | UNFIRED |
| Cont. 3-1 | CARBONATE | 0.1 | | | |
| Ex. 3-2 | | 0.1 | 0.5 | 1 | |
| Cont. 3-2 | | 0.1 | | 1 | |
| Ex. 4-1 | HYDROXY- | 1 | 1 | | UNFIRED |
| Cont. 4-1 | APATITE | 1 | | | |
| Ex. 4-2 | | 1 | 1 | 3 | |
| Cont. 4-2 | | 1 | | 3 | |
| Ex. 4-3 | | 1 | 1 | | 1000° C. |
| Cont. 4-3 | | 1 | | | |
| Ex. 4-4 | | 1 | 1 | 3 | |
| Cont. 4-4 | | 1 | | 3 | |
| Ex. 5-1 | CALCIUM | 2 | 2 | | UNFIRED |
| Cont. 5-1 | TERTIARY | 2 | | | |
| Ex. 5-2 | PHOSPHATE | 2 | 2 | 2 | |
| Cont. 5-2 | | 2 | | 2 | |
| Ex. 5-3 | | 2 | 2 | | 1200° C. |
| Cont. 5-3 | | 2 | | | |
| Ex. 5-4 | | 2 | 2 | 2 | |
| Cont. 5-4 | | 2 | | 2 | |
| Ex. 6-1 | CALCIUM | 2 | 2 | | UNFIRED |
| Cont. 6-1 | SECONDARY | 2 | | 2 | |
| Ex. 6-2 | PHOSPHATE | 2 | 2 | 2 | |
| Cont. 6-2 | | 2 | | | |
| Ex. 6-3 | | 2 | 2 | | 1200° C. |
| Cont. 6-3 | | 2 | | | |
| Ex. 6-4 | | 2 | 2 | 2 | |
| Cont. 6-4 | | 2 | | 2 | |
| Ex. 7-1 | CALCIUM | 2 | 2 | | UNFIRED |
| Cont. 7-1 | PYRO- | 2 | | | |
| Ex. 7-2 | PHOSPHATE | 2 | 2 | 2 | |
| Cont. 7-2 | | 2 | | 2 | |
| Ex. 7-3 | | 2 | 2 | | 1200° C. |
| Cont. 7-3 | | 2 | | | |
| Ex. 7-4 | | 2 | 2 | 2 | |
| Cont. 7-4 | | 2 | | 2 | |
| Ex. 8-1 | HYDROXY- | 5 | 3 | | UNFIRED |
| Cont. 8-1 | APATITE | 5 | | | |
| Ex. 8-2 | | 5 | 3 | 3 | |
| Cont. 8-2 | | 5 | | 3 | |
| Ex. 8-3 | | 5 | 3 | | 1200° C. |
| Cont. 8-3 | | 5 | | | |
| Ex. 8-4 | | 5 | 3 | 3 | |
| Cont. 8-4 | | 5 | | 3 | |
| Ex. 9-1 | CALCIUM | 10 | 4 | | UNFIRED |
| Cont. 9-1 | TERTIARY | 10 | | | |
| Ex. 9-2 | PHOSPHATE | 10 | 4 | 5 | |
| Cont. 9-2 | | 10 | | 5 | |
| Ex. 9-3 | | 10 | 4 | | 1200° C. |
| Cont. 9-3 | | 10 | | | |
| Ex. 9-4 | | | 10 | 4 | 5 |

TABLE 1-continued

| SAMPLE | CARRIER | AMOUNTS CARRIED (WT-%) | | | FIRING TEMPERATURE |
|---|---|---|---|---|---|
| | | Ag | Si | Zn | |
| Cont. 9-4 | | 10 | | 5 | |

TABLE 1

| SAMPLE | CARRIER | AMOUNTS CARRIED (WT-%) | | | FIRING TEMPERATURE |
|---|---|---|---|---|---|
| | | Ag | Si | Zn | |
| Ex. 1-1 | HYDROXY- | 0.0001 | | | UNFIRED |
| Cont. 1-1 | APATITE | 0.0001 | | | |
| Ex. 1-2 | | 0.0001 | | 0.5 | |
| Cont. 1-2 | | 0.0001 | | 0.5 | |
| Ex. 1-3 | | 0.0001 | | | 960° C. |
| Cont. 1-3 | | 0.0001 | | | |
| Ex. 1-4 | | 0.0001 | | 0.5 | |
| Cont. 1-4 | | 0.0001 | | 0.5 | |
| Ex. 2-1 | CALCIUM | 0.1 | 0.05 | | UNFIRED |
| Cont. 2-1 | TERTIARY | 0.1 | | | |
| Ex. 2-2 | PHOSPHATE | 0.1 | 0.005 | 0.005 | |
| Cont. 2-2 | | 0.1 | | 0.005 | |
| Ex. 2-3 | | 0.1 | 0.005 | | 1000° C. |
| Cont. 2-3 | | 0.1 | | | |
| Ex. 2-4 | | 0.1 | 0.005 | 0.005 | |
| Cont. 2-4 | | 0.1 | | 0.005 | |
| Ex. 3-1 | CALCIUM | 0.1 | 0.5 | | UNFIRED |
| Cont. 3-1 | CARBONATE | 0.1 | | | |
| Ex. 3-2 | | 0.1 | 0.5 | 1 | |
| Cont. 3-2 | | 0.1 | | 1 | |
| Ex. 4-1 | HYDROXY- | 1 | 1 | | UNFIRED |
| Cont. 4-1 | APATITE | 1 | | | |
| Ex. 4-2 | | 1 | 1 | 3 | |
| Cont. 4-2 | | 1 | | 3 | |
| Ex. 4-3 | | 1 | 1 | | 1000° C. |
| Cont. 4-3 | | 1 | | | |
| Ex. 4-4 | | 1 | 1 | 3 | |
| Cont. 4-4 | | 1 | | 3 | |
| Ex. 5-1 | CALCIUM | 2 | 2 | | UNFIRED |
| Cont. 5-1 | TERTIARY | 2 | | | |
| Ex. 5-2 | PHOSPHATE | 2 | 2 | 2 | |
| Cont. 5-2 | | 2 | | 2 | |
| Ex. 5-3 | | 2 | 2 | | 1200° C. |
| Cont. 5-3 | | 2 | | | |
| Ex. 5-4 | | 2 | 2 | 2 | |
| Cont. 5-4 | | 2 | | 2 | |
| Ex. 6-1 | CALCIUM | 2 | 2 | | UNFIRED |
| Cont. 6-1 | SECONDARY | 2 | | 2 | |
| Ex. 6-2 | PHOSPHATE | 2 | 2 | 2 | |
| Cont. 6-2 | | 2 | | | |
| Ex. 6-3 | | 2 | 2 | | 1200° C. |
| Cont. 6-3 | | 2 | | | |
| Ex. 6-4 | | 2 | 2 | 2 | |
| Cont. 6-4 | | 2 | | 2 | |
| Ex. 7-1 | CALCIUM | 2 | 2 | | UNFIRED |
| Cont. 7-1 | PYRO- | 2 | | | |
| Ex. 7-2 | PHOSPHATE | 2 | 2 | 2 | |
| Cont. 7-2 | | 2 | | 2 | |
| Ex. 7-3 | | 2 | 2 | | 1200° C. |
| Cont. 7-3 | | 2 | | | |
| Ex. 7-4 | | 2 | 2 | 2 | |
| Cont. 7-4 | | 2 | | 2 | |
| Ex. 8-1 | HYDROXY- | 5 | 3 | | UNFIRED |
| Cont. 8-1 | APATITE | 5 | | | |
| Ex. 8-2 | | 5 | 3 | 3 | |
| Cont. 8-2 | | 5 | | 3 | |
| Ex. 8-3 | | 5 | 3 | | 1200° C. |
| Cont. 8-3 | | 5 | | | |
| Ex. 8-4 | | 5 | 3 | 3 | |
| Cont. 8-4 | | 5 | | 3 | |
| Ex. 9-1 | CALCIUM | 10 | 4 | | UNFIRED |
| Cont. 9-1 | TERTIARY | 10 | | | |
| Ex. 9-2 | PHOSPHATE | 10 | 4 | 5 | |
| Cont. 9-2 | | 10 | | 5 | |
| Ex. 9-3 | | 10 | 4 | | 1200° C. |
| Cont. 9-3 | | 10 | | | |
| Ex. 9-4 | | 10 | 4 | 5 | |
| Cont. 9-4 | | 10 | | 5 | |

EXAMPLE 10

Test of Antibacterial Strength

A bacterial solution containing $4.7 \times 10^5$ colon bacilli was added to a phosphate buffer solution to which 1% by weight of each of the samples of Experiments 1) through 9) has been added, and the antibacterial strength against the colon bacilli was measured for each sample. The result of measurement was that absolutely no bacteria were detected in 24 hrs.

EXAMPLE 11

Test of Whiteness Degree

A spectrophotometer was used to measure the degree of whiteness of the powders of antibacterial calcium phosphate and antibacterial calcium carbonate produced in Examples 1) through 9). Barium sulfate was used as the standard substance. Also, as the control, ceramics of Controls 1) through 9) were produced. These ceramics were obtained by causing ceramics the same as those used in Examples 1) through 9) to carry silver and zinc and substantially were on a par with Examples 1) through 9) with the exception of the fact that silicon was deleted. These ceramics were measured for degree of whiteness. With regard to the heat-fired product, ceramics of Controls 1) through 9) were produced by heat-firing these ceramics at temperatures the same as those in Examples 1) through 9), and the degree of whiteness thereof was measured. Furthermore, the degree of whiteness of these samples was measured after letting them stand in a bright room for six months. The results are shown in Tables 2 and 3.

TABLE 2

| SAMPLE MEASURED VALUE | WHITENESS DEGREE | |
|---|---|---|
| | ORIGINAL POWDER | AFTER STANDING FOR 6 MOS. |
| Ex. 1-1 | 93.55 | 91.64 |
| Cont. 1-1 | 87.84 | 81.73 |
| Ex. 2-1 | 88.28 | 83.36 |
| Cont. 2-1 | 75.86 | 62.01 |
| Ex. 3-1 | 83.22 | 75.60 |
| Cont. 3-1 | 74.19 | 59.85 |
| Ex. 4-1 | 72.34 | 62.40 |
| Cont. 4-1 | 61.65 | 45.47 |
| Ex. 5-1 | 73.33 | 65.36 |
| Cont. 5-1 | 54.47 | 30.57 |
| Ex. 6-1 | 71.13 | 57.50 |
| Cont. 6-1 | 57.49 | 25.32 |
| Ex. 7-1 | 67.13 | 57.80 |
| Cont. 7-1 | 52.93 | 27.40 |
| Ex. 8-1 | 70.76 | 63.34 |
| Cont. 8-1 | 50.44 | <20 |
| Ex. 9-1 | 68.55 | 55.75 |
| Cont. 9-1 | 47.47 | <20 |
| Ex. 1-3 | 91.22 | 90.39 |
| Cont. 1-3 | 83.23 | 80.21 |
| Ex. 2-3 | 85.32 | 83.59 |
| Cont. 2-3 | 71.16 | 64.30 |
| Ex. 3-3 | | |
| Cont. 3-3 | | |
| Ex. 4-3 | 74.07 | 72.08 |
| Cont. 4-3 | 56.05 | 48.28 |
| Ex. 5-3 | 82.74 | 80.93 |
| Cont. 5-3 | 58.71 | 48.49 |
| Ex. 6-3 | 83.30 | 76.05 |
| Cont. 6-3 | 58.16 | 45.92 |
| Ex. 7-3 | 79.68 | 76.28 |
| Cont. 7-3 | 51.36 | 44.00 |
| Ex. 8-3 | 76.65 | 71.64 |
| Cont. 8-3 | 53.22 | 39.55 |
| Ex. 9-3 | 69.42 | 66.54 |

TABLE 2-continued

| SAMPLE MEASURED VALUE | WHITENESS DEGREE | |
|---|---|---|
| | ORIGINAL POWDER | AFTER STANDING FOR 6 MOS. |
| Cont. 9-3 | 51.52 | 35.97 |

TABLE 3

| SAMPLE MEASURED VALUE | WHITENESS DEGREE | |
|---|---|---|
| | ORIGINAL POWDER | AFTER STANDING FOR 6 MOS. |
| Ex. 1-2 | 94.25 | 92.17 |
| Cont. 1-2 | 90.17 | 85.58 |
| Ex. 2-2 | 89.19 | 85.36 |
| Cont. 2-2 | 87.21 | 82.14 |
| Ex. 3-2 | 86.52 | 80.94 |
| Cont. 3-2 | 87.73 | 74.60 |
| Ex. 4-2 | 75.22 | 67.84 |
| Cont. 4-2 | 64.36 | 53.51 |
| Ex. 5-2 | 77.69 | 72.18 |
| Cont. 5-2 | 68.65 | 58.81 |
| Ex. 6-2 | 74.00 | 62.57 |
| Cont. 6-2 | 64.32 | 37.36 |
| Ex. 7-2 | 72.68 | 63.28 |
| Cont. 7-2 | 60.06 | 36.87 |
| Ex. 8-2 | 71.39 | 66.89 |
| Cont. 8-2 | 61.20 | 33.20 |
| Ex. 9-2 | 72.42 | 62.53 |
| Cont. 9-2 | 61.82 | 40.31 |
| Ex. 1-4 | 94.52 | 93.75 |
| Cont. 1-4 | 86.24 | 84.47 |
| Ex. 2-4 | 87.77 | 86.33 |
| Cont. 2-4 | 82.70 | 79.15 |
| Ex. 3-4 | | |
| Cont. 3-4 | | |
| Ex. 4-4 | 92.13 | 90.62 |
| Cont. 4-4 | 68.76 | 63.27 |
| Ex. 5-4 | 93.61 | 92.31 |
| Cont. 5-4 | 79.26 | 77.24 |
| Ex. 6-4 | 88.64 | 83.22 |
| Cont. 6-4 | 76.01 | 67.33 |
| Ex. 7-4 | 84.15 | 83.30 |
| Cont. 7-4 | 69.66 | 66.18 |
| Ex. 8-4 | 91.07 | 88.54 |
| Cont. 8-4 | 67.11 | 61.87 |
| Ex. 9-4 | 88.18 | 88.76 |
| Cont. 9-4 | 64.90 | 60.55 |

As a result of the foregoing, it will be understood that a calcium phosphate ceramic and calcium carbonate carrying silicon in addition to silver has outstanding effects in terms of degree of whiteness and resistance to discoloration.

What is claimed is:

1. An antibacterial ceramic material comprising a calcium phosphate ceramic containing an amount of silver from 0.0001 to 10% by weight with respect to the calcium phosphate ceramic, and at least 5% by weight of silicon with respect to the amount of silver.

2. An antibacterial ceramic material comprising calcium carbonate containing an amount of silver from 0.0001 to 10% by weight with respect to the calcium carbonate, and at least about 5% by weight of silicon with respect to the amount of silver.

3. An antibacterial ceramic material comprising a calcium phosphate ceramic containing an amount of silver from 0.001 to 10% by weight with respect to the calcium phosphate ceramic, at least 5% by weight of silicon with respect to the amount of silver, and at least 5% by weight of zinc with respect to the amount of silver.

4. An antibacterial ceramic material comprising calcium carbonate containing an amount of silver from 0.001 to 10% by weight with respect to the calcium carbonate, at least 5% by weight of silicon with respect to the amount of silver, and at least 5% by weight of zinc with respect to the amount of silver.

5. An antibacterial ceramic material of claims 1 or 3 wherein said calcium phosphate ceramic is calcium tertiary phosphate.

6. An antibacterial ceramic material of claims 1 or 3 wherein said calcium phosphate ceramic is hydroxyapatite.

7. An antibacterial ceramic material of claims 1 or 3, wherein said calcium phosphate ceramic is calcium secondary phosphate.

8. An antibacterial ceramic material of claims 1 or 3 wherein said calcium phosphate ceramic is calcium pyrophosphate.

9. An antibacterial ceramic material of claims 1 or 3 wherein the ceramic is heat-fired to a temperature of not less than 960° C.

* * * * *